United States Patent [19]

Kanner

[11] Patent Number: 5,250,266
[45] Date of Patent: Oct. 5, 1993

[54] CONTACT LENS CASE VENTING SYSTEM

[75] Inventor: Rowland W. Kanner, Guntersville, Ala.

[73] Assignee: Ciba Vision Corporation, Duluth, Ga.

[21] Appl. No.: 869,870

[22] Filed: Apr. 16, 1992

Related U.S. Application Data

[63] Continuation of Ser. No. 621,351, Nov. 30, 1990.

[51] Int. Cl.$^5$ .................... B65D 51/16; G05D 16/00; A61L 2/00
[52] U.S. Cl. .................... 422/113; 422/117; 422/301; 206/5.1; 220/209; 134/901
[58] Field of Search ............ 422/113, 117, 297, 300, 422/301; 206/5.1; 220/209

[56] References Cited

U.S. PATENT DOCUMENTS

| | | | |
|---|---|---|---|
| 3,406,862 | 10/1968 | Donaldson | 220/209 |
| 3,527,376 | 9/1970 | Young, Jr. | 220/209 |
| 4,396,583 | 8/1983 | LeBoeuf | 422/301 |
| 4,637,919 | 1/1987 | Ryder et al. | 422/300 |
| 4,672,996 | 6/1987 | Floyd et al. | 137/522 |
| 4,750,610 | 6/1988 | Ryder | 206/5.1 |
| 4,889,693 | 12/1989 | Su et al. | 422/113 |
| 4,956,156 | 9/1990 | Kanner et al. | 422/300 |
| 4,996,027 | 2/1991 | Kanner | 422/113 |

Primary Examiner—Robert J. Warden
Assistant Examiner—T. A. Trembley
Attorney, Agent, or Firm—Trexler, Bushnell, Giangiorgi & Blackstone, Ltd.

[57] ABSTRACT

An appliance for disinfecting contact lenses or the like wherein the lenses are disposed within a disinfecting solution which liberates the gas during the disinfecting action, includes a container body for immersion of the lenses within the disinfecting solution and a removable cap closing the container body. The appliance further includes a normally closed vent conduit for passage of the pressurized affluent gas from the container body through the cap, and within the vent conduit is a check valve including a disc member having a slit therethrough which opens for vent discharge of the gas with sufficient pressure on the disc exerted by the gas during passage through the vent conduit, after which the slit recloses to vent any subsequent leakage of the solution therethrough. In a preferred embodiment, the venting disc is clamped between upper and lower portions of the cap, so that the lower cap portion provides a supporting seat against which the closed slit is engaged and from which the slit disengages and opens to form a one-way venting valve. Passageways through the lower cap portion provide passage of the pressurized gas against the valve disc and with exertion of sufficient gas pressure, the disc slit opens to the venting gas discharged.

4 Claims, 1 Drawing Sheet

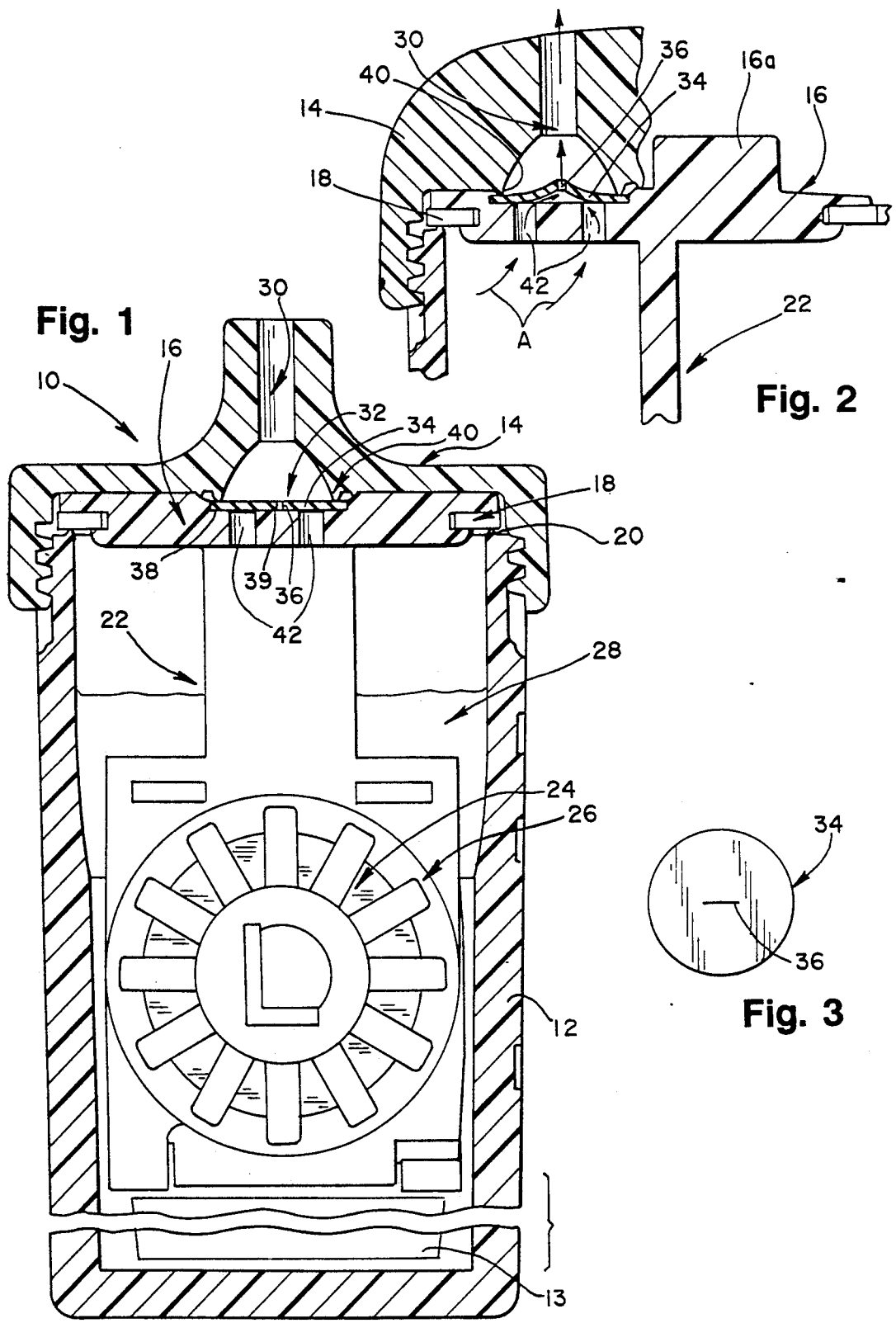

CONTACT LENS CASE VENTING SYSTEM

This application is a continuation of application Ser. No. 07/621,351, filed Nov. 30, 1990.

BACKGROUND OF THE INVENTION

This invention relates to container appliances for chemical sterilization of small articles such as contact lenses, and more particularly, relates to pressure relief venting of such appliances.

The well-known, commercialized contact lens disinfection process employing hydrogen peroxide solution as a bactericide is described for example in U.S. Pat. Nos. 4,750,610; 4,889,7693; and 4,956,156. In such process, the contact lenses are immersed overnight in an aqueous solution of hydrogen peroxide which is catalytically decomposed during the sterilization process resulting in liberation of oxygen gas. As a result, the liberated oxygen produces a pressure increase within the disinfecting vessel which is accordingly provided with venting structure for relief of the pressure to the ambience. The present invention provides simplified reliable, venting structure in such pressurized vessels particularly for low pressure discharge of the gas. The invention would of course be usable with any disinfecting process wherein a gaseous material is liberated during the process.

SUMMARY OF THE INVENTION

In accordance with the present invention, an appliance for disinfecting contact lenses or the like wherein the lenses are disposed within a disinfecting solution which liberates the gas during the disinfecting action, includes a container body for immersion of the lenses within the disinfecting solution and a removable cap closing the container body. The appliance further includes a normally closed vent conduit for passage of the pressurized affluent gas from the container body through the cap, and within the vent conduit is a check valve including a disc member having a slit therethrough which opens for vent discharge of the gas with sufficient pressure on the disc exerted by the gas during passage through the vent conduit, after which the slit recloses to vent any subsequent leakage of the solution therethrough.

In a preferred embodiment, the venting disc is clamped between upper and lower portions of the cap, so that the lower cap portion provides a supporting seat against which the closed slit is engaged and from which the slit disengages and opens to form a one-way venting valve. Passageways through the lower cap portion provide passage of the pressurized gas against the valve disc and with exertion of sufficient gas pressure, the disc slit opens to the venting gas discharged.

BRIEF DESCRIPTION OF THE DRAWINGS

FIG. 1 is a sectional view of one embodiment of a lens sterilizing appliance in accordance with the present invention;

FIG. 2 is a fragmentary sectional view taken from FIG. 1 illustrating passage of gas through an opened check valve formed in the cap of the appliance; and FIG. 3 is a plan view of the check valve disc shown in FIGS. 1 and 2.

DETAILED DESCRIPTION OF THE ILLUSTRATED EMBODIMENT

Referring now in more detail to FIGS. 1 and 2, one embodiment of the contact lens disinfecting appliance in accordance with the present invention is generally designated by reference character 10. The appliance 10 includes a generally cylindrical container body 12 having a threaded end opening for receiving a removable screw cap 14. As best shown in FIGS. 1 and 2, a lower portion of cap 14 includes a closure flange 16 having an upwardly projecting tongue 16a which is secured in a mating mortise, for example, by sonic welding. The closure disc or flange 16 has a grooved periphery within which an annular gasket 18 is secured. The gasket 18 seals against the end rim 20 at the opening of the container body 12. A depending lens-supporting frame 22 is secured to and projects downwardly into the cavity within the cylindrical container body 12 when the cap 14 is mounted thereon. A pair of contact lenses 24 are enclosed and supported by the frame 22 and respective pivotal baskets 26 (one of which is illustrated) as more fully described in U.S. Pat. No. 4,750,610, the text of which is incorporated by reference herein. The baskets 26 are perforated to allow passage of the disinfecting liquid such as hydrogen peroxide solution 28 within which the lenses 24 are immersed.

In the disinfecting process, the hydrogen peroxide solution is poured into the container body 12 and the cap 14 is threaded thereon to seal the gasket 18 against the rim 20 as shown in FIG. 1, thereby immersing the lenses 24 within the solution. A catalytic element 13 initiates decomposition of the hydrogen peroxide solution and as the disinfecting reaction proceeds, the liberated oxygen exerts progressively elevated pressure within the container body 12.

In order to vent the elevated pressure generated within the container body 12, the cap 14 is provided with a vent passageway 30 which opens through the top of the cap 14 and a venting check valve structure generally designated by reference character 32 which leads from the interior of the container body to the vent passageway 30. The check valve structure 32 includes a valve disc 34 with a generally centrally located slit 36 as best shown in FIG. 3. The disc 34 is seated on a recess 38 formed within the cap flange 16. As best shown in FIG. 2, the vent structure 32 and passageway 30 are offset in relation to the centrally positioned lens support frame 22. The disc 34 is peripherally clamped against the flange recess 38 by an overlying ring 40 which is molded to downwardly project from the upper portion of the cap 14.

As best shown in FIG. 1, the normally closed valve slit 36 is seated upon the central surface 39 of the seating recess 38 which also has a plurality of vent ports 42 which pass through the cap flange 16 and open against the valve disc 34 spaced from the valve slit 36.

When the elevated pressure of the liberated oxygen gas is communicated through the ports 42 against the disc 34 as shown in FIG. 2, the upwardly directed gas flow indicated by arrows A will lift and upwardly deflect the central portion of the disc 34 to open the slit 36 allowing passage of the gas upwardly through the open slit leading to the passageway 30 and discharge therefrom to the ambience. Following gas discharge to sufficiently reduce the pressure within the container 12, the deflected central portion of the disc 34 will downwardly redeflect to reclose the slit 36 against the surface 39 of the recess 38 again in the position shown in FIG. 1 so that the closed slit will prevent any subsequent leakage of solution or entry of air. The slitted disc 34 functions as a one-way check valve and allows only vent discharge of pressurized gas. As a result, the closed slit also prevents any backflow and entry of bacterial or other contamination into the interior of the container, while automatically opening to vent subsequently generated excessive gas pressure.

The valve disc 34 can be fabricated, for example, from typical elastomeric composition such as silicone rubber. In typical lens sterilization containers, a silicone rubber disc in a grade of 50 durometer and dimensioned approximately 0.30 inch in diameter and 0.030 inch thick with a slit of approximately 0.060 inch has performed to open at a threshold pressure in the range of approximately 6-8 psig and enabled a vent gas flow rate of approximately 30 cc's per minute at pressures of approximately 25 psig.

While particular embodiments of the present invention have been described herein, it will be obvious to those skilled in the art that changes and modifications in various aspects may be made without departing from the broad scope of the invention. Consequently, the scope of the invention is not limited by any particular embodiment but is defined by the appended claims and the equivalents thereof.

The invention is claimed as follows:

1. An appliance for disinfecting contact lenses or the like wherein the lenses are disposed within a disinfecting solution which liberates a gas during the disinfecting process, said appliance comprising:
   a) a container body including an opening therefrom;
   b) a removable cap means closing said opening;
   c) a normally closed vent conduit for passage of pressurized effluent gas from said container body through said removable cap; and
   d) a check valve in said normally closed vent conduit including a disc member having a linear slit therethrough which closes on itself and which opens for vent discharge of said pressurized effluent gas by sufficient pressure on said disc member exerted by said pressurized effluent gas during passage through said normally closed vent conduit, after which said linear slit recloses to prevent any subsequent leakage of any disinfecting solution therethrough, wherein said removable cap means includes a non-cylindrical supporting surface against which said closed slit is engaged when closed, and from which said slit disengages when opened to form a one-way venting valve.

2. An appliance according to claim 1 wherein said removable cap means comprises upper and lower cap portions and wherein said supporting surface is formed within a recess in said lower cap portion.

3. An appliance according to claim 1 wherein said disc member has a generally circular configuration and said linear slit is linearly aligned along a diameter of said disc member at a generally central location therein.

4. An appliance according to claim 1, wherein said supporting surface against which said closed slit is engaged is planar.

* * * * *

UNITED STATES PATENT AND TRADEMARK OFFICE
CERTIFICATE OF CORRECTION

PATENT NO. : 5,250,266
DATED : October 5, 1993
INVENTOR(S) : Rowland W. Kanner

It is certified that error appears in the above-indentified patent and that said Letters Patent is hereby corrected as shown below:

Column 1, Line 15 " 4,889,7693 "  should be  — 4,889,693

Signed and Sealed this

Thirty-first Day of May, 1994

Attest:

BRUCE LEHMAN

*Attesting Officer*        *Commissioner of Patents and Trademarks*